US00PP20122P2

(12) United States Plant Patent
Van Zanten

(10) Patent No.: US PP20,122 P2
(45) Date of Patent: Jun. 23, 2009

(54) ***IRESINE* PLANT NAMED 'AUREO M'**

(50) Latin Name: *Iresine herbstii*
Varietal Denomination: Aureo M

(75) Inventor: Leo Van Zanten, Oxnard, CA (US)

(73) Assignee: Grolink Plant Company, Oxnard, CA (US)

( * ) Notice: Subject to any disclaimer, the term of this patent is extended or adjusted under 35 U.S.C. 154(b) by 40 days.

(21) Appl. No.: 11/823,299

(22) Filed: Jun. 27, 2007

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Wendy C. Haas

(57) ABSTRACT

A new and distinct *Iresine* plant cultivar is disclosed, characterized by a distinct leaf color of dark purple foliage with magenta veins; magenta petiole and stems; strong stems; and an upright growth habit.

1 Drawing Sheet

Latin name of the genus and species: *Iresine herbstii.*
Variety denomination: 'AUREO M'.

BACKGROUND OF THE INVENTION

The new cultivar is the product of an induced mutation. Aureo M was discovered as a single plant by Leo van Zanten in March 2005 in a cultivated area of Oxnard, Calif. in a greenhouse. Two thousand unrooted cuttings from *Iresine herbstii brilliantissima* were irradiated with gamma rays at a dose of 25 Gy. The treated cuttings were planted for rooting and growing. Subsequent selection among the population resulted in the discovery as a single plant of this new variety.

Asexual reproduction of the new cultivar 'AUREO M' by terminal cuttings was performed in Oxnard, Calif. and has shown that the unique features of this cultivar are stable and reproduced true to type on successive generations.

SUMMARY OF THE INVENTION

The cultivar 'AUREO M' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'AUREO M.' These characteristics in combination distinguish 'AUREO M' as a new and distinct *Iresine* cultivar:

1. Distinct leaf color of light magenta with darker purple veins;
2. Magenta petiole and stems;
3. Strong stems; and
4. Upright growth habit.

Plants of the new cultivar 'AUREO M' are similar to plants of the parent variety, *Iresine herbstii brilliantissima,* in most horticultural characteristics, however, plants of the new cultivar 'AUREO M' have an upright growth habit compared to the compact growth habit of the parent. Additionally, the petiole and stems of 'AUREO M' are magenta compared to the dark purple of the parent variety. Finally, the longevity of 'AUREO M' is several weeks longer.

In comparison to the variety 'AUREO LG' (U.S. Plant patent application No. 11/823,297), 'AUREO M' has light magenta and dark purple colored foliage compared to the lime green foliage of 'AUREO LG'.

BRIEF DESCRIPTION OF THE PHOTOGRAPH

The accompanying photograph in the drawing illustrates in full color a typical plant of 'AUREO M' grown in a 2 gallon container. One cutting was used in the pot. The colors are as nearly true as is reasonably possible in a color representative of this type.

DETAILED BOTANICAL DESCRIPTION

In the following description, color references are made to The Royal Horticultural Society Colour Chart except where general terms of ordinary dictionary significance are used. The following observations and measurements describe 'AUREO M' plants grown in Oxnard, Calif. during the months of January through April. The growing temperature ranged from 12° C. to 15° C. at night to 12° C. to 20° C. during the day. Measurements and numerical values represent averages of typical plant types.

Botanical classification: *Iresine herbstii* cultivar 'AUREO M.'
Commercial classification: Bloodleaf.

PROPAGATION

Time to initiate roots: 12 days at 22–25° C.
Time to develop roots: 17 days at 22–25° C.
Root Description: Fine, fibrous, white in color.

PLANT

Plant type: Annual.
Growth habit: Upright.
Height: Approximately 47 cm.
Plant spread: Approximately 30 cm.
Growth rate: Moderate.
Branching characteristics: Opposite, decussate.
Number of lateral branches per plant: 7.
Length of lateral branches: Approximately 36 cm.

Diameter of lateral branches: Approximately 0.5 cm.
Number of leaves per lateral branch: Approximately 42.
Stem and stem base strength: Strong.
Stem Texture: Lightly pubescent.
Stem habit: Ascending.
Age of plant described: Approximately 98 days.

FOLIAGE

Leaf.
*Arrangement.*—Opposite.
*Average length.*—Approximately 5.7 cm.
*Average width.*—Approximately 4.5 cm.
*Shape of blade.*—Ovate to ovate lanceolate.
*Apex.*—Acuminate.
*Base.*—Oblique.
*Attachment.*—Petiolate.
*Margin.*—Cleft.
*Texture of top surface.*—Lightly pubescent.
*Texture of bottom surface.*—Lightly pubescent.
*Leaf internode length.*—Approximately 4.6 cm.
Color:
Developing foliage on the upper surface:
*Towards the margins.*—Near Red-Purple 59B.
*Center.*—Near Purple 79A.
*Towards the base.*—Near Purple 79A.
*Venation.*—Near Red-Purple 58A.
Developing foliage on the lower surface:
*Towards the margins.*—Near Red-Purple 59B.
*Center.*—Near Purple 79A.
*Towards the base.*—Near Purple 79A.
*Venation.*—Near Red-Purple 58A.
Fully expanded foliage on the upper surface:
*Towards the margins.*—Near Purple 79A.
*Towards the center.*—Near Red-Purple 59A.
*Center.*—Near Red-Purple 59A.
*Towards the base.*—Near Red-Purple 59A.
*Venation.*—Near Red-Purple 58A.
Fully expanded foliage on the lower surface:
*Towards the margins.*—Near Purple 79A.
*Towards the center.*—Near Red-Purple 59A.
*Center.*—Near Red-Purple 59A.
*Towards the base.*—Near Red-Purple 59A.
*Venation.*—Near Red-Purple 58A.
Petiole:
*Average length.*—Approximately 2.9 cm.
*Color.*—Near Red-Purple 58A.
*Diameter.*—Approximately 0.3 cm.

FLOWER No flower development has been observed on 'AUREO M.'

OTHER CHARACTERISTICS

Disease resistance: Neither resistance nor susceptibility to diseases or pests has been observed in this variety.
Drought tolerance/cold tolerance: Plants are hardy in the approximate range of 3° C. to −6° C., depending upon duration of cold and amount of moisture in the soil. With adequate water plants are hardy to a high temperature of 45° C.
Fruit/seed production: Not observed because commercially the plants are discarded or the flowers removed before seed set occurs.

What is claimed is:

1. A new and distinct cultivar of *Iresine* plant named 'AUREO M' as herein illustrated and described.

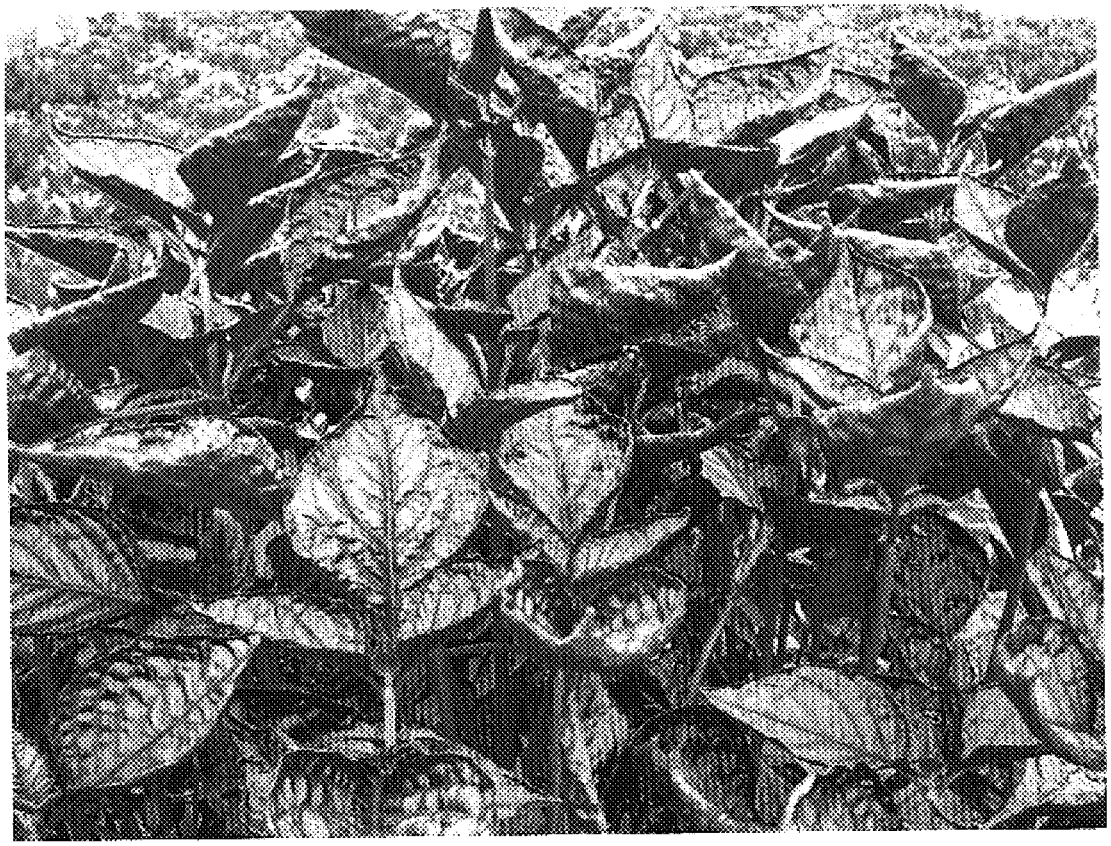

* * * * *